US010509047B2

(12) United States Patent
Pedain

(10) Patent No.: US 10,509,047 B2
(45) Date of Patent: Dec. 17, 2019

(54) METHOD FOR HANDLING A SAMPLE TUBE AND HANDLING DEVICE

(71) Applicant: Roche Diagnostics Operations, Inc., Indianapolis, IN (US)

(72) Inventor: Christoph Pedain, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/990,854

(22) Filed: Jan. 8, 2016

(65) Prior Publication Data

US 2016/0124006 A1    May 5, 2016

Related U.S. Application Data

(63) Continuation of application No. PCT/EP2014/066070, filed on Jul. 25, 2014.

(30) Foreign Application Priority Data

Jul. 26, 2013    (DE) .................. 10 2013 214 694

(51) Int. Cl.
| | | |
|---|---|---|
| *G01N 35/00* | (2006.01) | |
| *G01B 11/00* | (2006.01) | |
| *B25J 9/16* | (2006.01) | |
| *G01N 35/04* | (2006.01) | |

(52) U.S. Cl.
CPC ...... *G01N 35/00584* (2013.01); *B25J 9/1612* (2013.01); *B25J 9/1697* (2013.01); *G01B 11/002* (2013.01); *G01N 35/0099* (2013.01); *G01N 2035/0493* (2013.01)

(58) Field of Classification Search
CPC ..... B25J 9/1612; B25J 9/1697; G01B 11/002; G01N 2035/0493; G01N 35/00584; G01N 35/009
See application file for complete search history.

(56) References Cited

U.S. PATENT DOCUMENTS

| | | | |
|---|---|---|---|
| 5,741,171 A | | 4/1998 | Sarfaty et al. |
| 6,293,750 B1 * | | 9/2001 | Cohen ................ G01N 35/0099 |
| | | | 414/744.4 |
| 9,574,219 B2 | | 2/2017 | Ronsick et al. |
| 2002/0102736 A1 * | | 8/2002 | Kittock .................... B25J 15/12 |
| | | | 436/48 |
| 2009/0025502 A1 | | 1/2009 | Nakamoto |
| 2010/0018330 A1 | | 1/2010 | Marty et al. |

(Continued)

FOREIGN PATENT DOCUMENTS

| | | |
|---|---|---|
| DE | 102006027680 A1 | 12/2007 |
| EP | 1466161 B1 | 10/2004 |

(Continued)

OTHER PUBLICATIONS

Screenshot of position as synonym for orientation. Google searched "orientation" on Jun. 14, 2017.*

(Continued)

*Primary Examiner* — Benjamin R Whatley
(74) *Attorney, Agent, or Firm* — Roche Diagnostics Operations, Inc.

(57) ABSTRACT

A method and a device for handling sample tubes are presented. A position of the sample tube is identified and the sample tube is handled depending thereon.

15 Claims, 1 Drawing Sheet

(56) References Cited

U.S. PATENT DOCUMENTS

| | | | |
|---|---|---|---|
| 2010/0250010 A1* | 9/2010 | Ferrara | G01N 25/4866 700/279 |
| 2011/0106312 A1* | 5/2011 | Chen | B25J 9/1697 700/259 |
| 2012/0165986 A1* | 6/2012 | Fuhlbrigge | B25J 9/1687 700/259 |
| 2013/0028697 A1* | 1/2013 | Neeper | G01N 35/0099 414/751.1 |
| 2013/0034410 A1 | 2/2013 | Heise et al. | |
| 2013/0065797 A1* | 3/2013 | Silbert | G01F 23/265 506/39 |
| 2013/0129166 A1* | 5/2013 | Muller | B01D 21/262 382/128 |
| 2013/0149079 A1* | 6/2013 | Ohiso | B25J 9/026 414/222.13 |
| 2013/0208105 A1* | 8/2013 | Schmidt | G01N 21/9054 348/92 |
| 2013/0280143 A1* | 10/2013 | Zucchelli | B01L 3/0237 422/501 |
| 2014/0100694 A1 | 4/2014 | Rueckl et al. | |
| 2016/0025756 A1* | 1/2016 | Pollack | G01N 35/04 436/47 |
| 2017/0350878 A1 | 12/2017 | Holmes et al. | |

FOREIGN PATENT DOCUMENTS

| | | | |
|---|---|---|---|
| JP | 2001-315079 A | 11/2001 | |
| JP | 2003-177009 A | 6/2003 | |
| JP | 2003-177099 | 6/2003 | |
| JP | 2008-068348 A | 3/2008 | |
| JP | 2009-269110 A | 11/2009 | |
| JP | 2009-279706 A | 12/2009 | |
| JP | 2010-152664 A | 7/2010 | |
| WO | WO-2012019701 A1 * | 2/2012 | G01N 21/9054 |
| WO | 2012/069925 A1 | 5/2012 | |
| WO | 2013/070744 A2 | 5/2013 | |
| WO | 2013/070754 A1 | 5/2013 | |

OTHER PUBLICATIONS

International Search Report dated Apr. 9, 2015, in Application No. PCT/EP2014/066070, 2 pages.

* cited by examiner

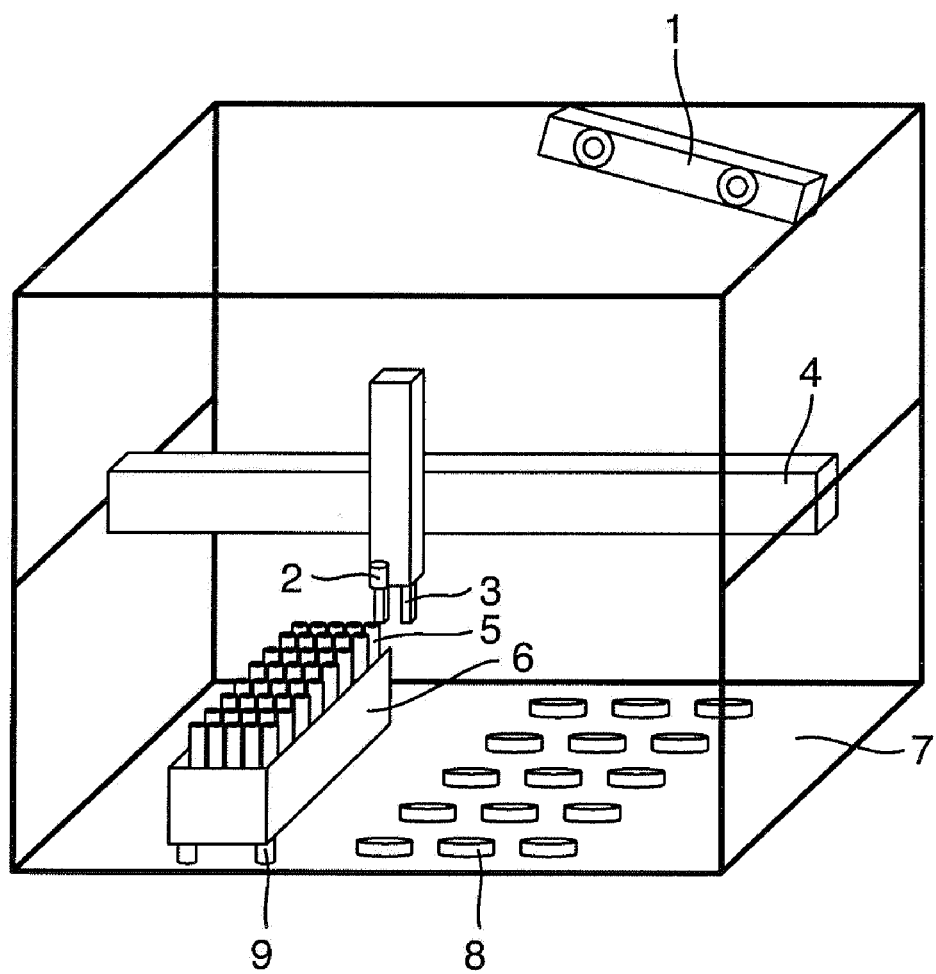

METHOD FOR HANDLING A SAMPLE TUBE AND HANDLING DEVICE

CROSS-REFERENCE TO RELATED APPLICATIONS

This application is a continuation of PCT/EP2014/066070, filed Jul. 25, 2014, which is based on and claims priority to DE 10 2013 214 694.9 filed Jul. 26, 2013, which is hereby incorporated by reference.

BACKGROUND

The present disclosure generally relates to a method and device for handling a sample tube by a gripper apparatus Known methods and devices are often used to change the location of sample tubes filled with samples. By way of example, this may be necessary if sample tubes filled with a substance to be analyzed are intended to be moved into an analyzer or if reformatting is necessary, which typically means the transfer of the sample tubes from a holding apparatus such as a carrier into a holding apparatus of a different type.

Known devices and methods are typically configured in such a way that the gripper apparatus is controlled electronically, i.e., to be precise in such a way that positions for receiving and setting down sample tubes are known and stored in a coordinate system, and so the gripper apparatus can directly approach these stored positions. However, this makes reacting to unpredicted changes in the position or in an alignment of the respective sample tube more difficult. By way of example, if a sample tube slips, the gripper apparatus may grip the wrong position and therefore damage the sample tube. Moreover, erroneous gripping processes can increase the time required for the handling Therefore, there is a need to provide a device and method for handling a sample tube and/or a holder of the sample tube that can enable flexible handling, particularly for the case where the sample tubes to be handled are not always exactly aligned.

SUMMARY

According to the present disclosure, a device and method for automated handling of a sample tube by a gripper apparatus are presented. The sample tube can be filled with liquid to be analyzed. The method can comprise determining a position of the sample tube in space and handling the sample tube depending on the determined position by gripping the sample tube at the determined position by the gripper apparatus.

Accordingly, it is a feature of the embodiments of the present disclosure to provide a device and method for handling a sample tube and/or a holder of the sample tube that can enable flexible handling, particularly for the case where the sample tubes to be handled are not always exactly aligned. Other features of the embodiments of the present disclosure will be apparent in light of the description of the disclosure embodied herein.

BRIEF DESCRIPTION OF THE SEVERAL VIEWS OF THE DRAWING

The following detailed description of specific embodiments of the present disclosure can be best understood when read in conjunction with the following drawing, where like structure is indicated with like reference numerals and in which:

FIG. 1 illustrates a device for handling sample tubes by which it is also possible to perform a method for handling sample tubes according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for handling a sample tube by a gripper apparatus is presented. The method can comprise determining (establishing, identifying) a position of and/or an extent of and/or spatial information about the sample tube and/or the holder thereof in space and handling the sample tube and/or the holder thereof depending on the identified position or extent or spatial information.

In the method, the position of the sample tube can initially be determined, before handling of the sample tube is commenced. As a result, it can be possible to account for unpredicted and/or unplanned changes in the position in relation to a possibly predetermined or stored reference position. By way of example, the gripper apparatus can grip at exactly one position, at which a sample tube was identified. Delays or damage can be effectively avoided in this manner.

The gripper apparatus can be controlled, to be precise; it can be controlled electronically in an automatic manner. This can enable a simple implementation and simple programming and the provision of numerous functionalities.

The position can be a coordinate in a one-dimensional, two-dimensional or three-dimensional coordinate system. The number of dimensions to be considered can be predetermined by the technical conditions. To the extent that, for example, the gripper apparatus can merely be displaced in one dimension, the specification of one coordinate in a one-dimensional coordinate system can suffice. If the gripper apparatus is displaceable in two dimensions, for example with the aid of an XY-positioner, two coordinates in a two-dimensional coordinate system may be required. If the gripper apparatus is displaceable in three dimensions, for example with the aid of a robot arm, three coordinates in a three-dimensional coordinate system can generally be required. It is understood that further degrees of freedom can be provided in the gripper apparatus, even when using a one-dimensional or two-dimensional coordinate system for establishing a position and for controlling the gripper apparatus. By way of example, an additional degree of freedom in the vertical direction may be added to this, meaning that the gripper apparatus can be lowered and raised. However, when using a coordinate system with less than three dimensions, this degree of freedom can be controlled independently of an identified sample tube.

By way of example, positions at which the sample tubes can be situated or at which they can be set down, can be predetermined by an employed holding apparatus, such as a rack or a stand, with a plurality of such positions for receiving and holding sample tubes.

The gripper apparatus can be a conventional embodiment, for example in the form of pliers. Here, the gripper apparatus can be configured in such a way that it can grip the respective sample tubes and change the location thereof. However, the gripper apparatus can also have a completely different embodiment depending on how the respective sample tubes can be handled. By way of example, the gripper apparatus can comprise a magnet or an opening to which negative pressure can be applied for suctioning-on sample tubes.

The sample tube can form a liquid container, which can be held in a puck. The puck can be a disk which can typically comprise a holder for a sample tube. By way of example, this holder can be configured in the form of a depression which can be formed centrally in the puck. Then, a sample tube can be stuck into this depression. A puck can advantageously comprise a permanent magnet which can enable a displacement of the puck on a base configured for this by the application of magnetic fields. The sample tubes can typically be conventional sample tubes for receiving liquids, as are used in the medical or chemical sectors. They can have a sealable opening.

The liquid container can be filled with a liquid to be analyzed. Here, this can be, for example, a bodily fluid such as blood or urine. Therefore, the method can be applicable for medical purposes. In the field of medical technology, there can often be analyses which can be intended to be carried out in succession for a plurality of samples. In this case, the method can significantly reduce the overall processing time and avoid possible errors and delays.

During the handling of the sample tube, the sample tube can be changed in terms of its location and, to this end, can (also) be lifted. This can enable the displacement of the sample tube to a different position. By lifting, the sample tube can for example be removed from a holding apparatus (rack). Likewise, it can subsequently be set down again in a different holding apparatus, or in the same holding apparatus.

The method can be used for reformatting. Here, it can be used for displacing sample tubes stored on a holding apparatus of a first type and intended to be transferred to a holding apparatus of a second type. Using this, it can be possible, for example, to "reformat" one group of sample tubes arranged in or on a specific holding apparatus, which was e.g. filled in a medical practice, to a different holding apparatus, which can be suitable for the introduction into an analysis instrument.

Further, during the determination of the position of the sample tube, a center point or an extent of the sample tube can be determined in relation to one, two or three dimensions. The identification of a center point can be advantageous, particularly in the case of sample tubes which have a certain symmetry, at least in one, two or three dimensions. By way of example, a center point in the form of a point on an axis of symmetry of the sample tube arranged at an upper end of the sample tube can be identified in the case of typical sample tubes with a cylindrical embodiment. Likewise, it can also be possible to identify e.g. an external extent in the case of such a sample tube, which may be particularly advantageous if it is to be expected that use is made of sample tubes with different extents. By way of example, if sample tubes with different diameters are used, the established extent of the sample tube can be taken into account during gripping by the gripper apparatus, which can avoid damage, for example as a result of excessive application of force in the case of a sample tube that has a thicker embodiment than assumed. The number of dimensions to be taken into account can depend on the respective conditions.

Furthermore, during the determination of the position of the sample tube, an alignment of the sample tube, for example an axis indicating the alignment, can be determined. As a result, the gripper apparatus can also consider alignments deviating from the standard. By way of example, this may occur if sample tubes are mounted obliquely in a holding apparatus. In this case, the gripper apparatus can for example likewise grip the sample tube obliquely and pull it out accordingly. This can also be used to avoid damage. To this end, the handling of the sample tube can furthermore be performed depending on the alignment of the sample tube.

The determination of the position of the sample tube can be performed using a stereo camera or a 3D camera. Such cameras can record not only a conventional two-dimensional image, but can also achieve a spatial resolution. To this end, these can typically be configured in such a way that the images of two two-dimensional cameras can be evaluated in parallel.

The determination of the position can furthermore be performed using a further camera, which can be a 2D camera and can be assembled on the gripper apparatus. This further camera can also be referred to as a gripper camera. By use of the further camera, it can be possible to increase the accuracy when gripping; in particular, it can be possible to once again record a sample tube with increased accuracy from a close distance in a position in which the gripper apparatus is situated immediately adjacently to this sample tube to be recorded. Using this, it can be possible to further optimize the gripping process. Incorrect gripping or damage to the sample tube can become even more improbable therewith.

In accordance with one embodiment, the method can comprise identifying a free position in a holding apparatus or set-down area for sample tubes, which can be performed using the determination of the position. A sample tube can subsequently be set down at the free position by the gripper apparatus.

What this can achieve is that, using the determination of the position, which can be e.g. configured as cameras, it can also be possible to establish the occupancy of a holding apparatus or transport area such that free positions can be identified. The free positions can subsequently be used for setting down sample tubes. Hence, the sample tubes can once again be securely held in a holding apparatus suitable therefor.

Alternatively, the identification of a free position can also be performed by (mechanical) scanning. This can be advantageous in specific situations.

Furthermore, during the identification of a free position, use can be made of an image database, namely for establishing target coordinates. By way of example, typical images of sample tubes can be stored in such an image database such that an appropriate evaluation can reliably and easily identify whether such a sample tube is situated in a position in which it can be arranged on account of the embodiment of an employed holding apparatus, for example. The image database can also store images of states during a handling process in order, for example, to store original occupancies and the like. The target coordinates can be used immediately for controlling the gripper. By way of example, these can be coordinates as already described further above.

The method can further comprise identifying damage of the sample tube which can be performed using the determination of the position and wherein the handling of the sample tube can be performed depending on whether damage was identified. Using this, it can also be possible to use the already available identification of the position, e.g. appropriate cameras, to identify possible damage to the sample tubes in good time. By way of example, to the extent that a sample tube is damaged, provision can be made for the gripping and raising of such a sample tube to be dispensed with. To the extent that, for example, a sample tube is merely damaged at an upper edge, this can prevent destruction of the sample tube being introduced by gripping by the gripper apparatus, which can be connected with the loss of a liquid to be analyzed.

Further, method can comprise setting down a sample tube at a position from which a sample tube was previously lifted. Expressed differently, the employed gripper apparatus can thus itself free up a position by virtue of a sample tube previously situated at the corresponding position being transferred to another position. By way of example, this can be used to force a specific arrangement or sorting of sample tubes in a holding apparatus.

A device for handling sample tubes is disclosed. The device can comprise a gripper apparatus, an image acquisition apparatus, and a control apparatus for controlling the gripper apparatus depending on signals generated by the image acquisition apparatus.

The device can achieve the advantages already described with reference to the method. The variants of the individual components already described with reference to the method can be applied accordingly to the device.

The control apparatus can be an electronic control apparatus. Such a control apparatus can comprise a processor and storage. Instructions can be stored in the storage. A method can be performed in the case of the execution of the instructions by the processor. Here, all variants of the method described above can be applied accordingly. The advantages described in this context can therefore be achieved with the aid of the device for handling sample tubes.

The image acquisition apparatus can comprise a stereo camera or a 3D camera arranged stationary in space. The image acquisition apparatus can further comprises a 2D camera arranged at the gripper apparatus and is displaced with the latter. Using this, it can be possible to achieve the advantages already described above.

The gripper apparatus can be displaceable by an XY-positioner. This can enable a simple displaceability in two dimensions, which can be a suitable configuration for the most typical applications, in which samples to be analyzed are to be taken from appropriate holding apparatuses and transferred back therein.

By way of example, spatial information about a tube arrangement can be determined by a camera. A controller of a gripper can then perform a grip depending on the spatial information. To this end, a 3D spatial measurement can be performed using a stereo camera. To the extent that the gripper can also take the alignment of tubes into consideration in the process, the alignment of a tube may not need to exactly correspond to a predetermined alignment. Rather, a tube can also stick obliquely in a holding apparatus, such as e.g. a rack, as this is identified by a camera and appropriately compensated for by the gripper.

By way of example, provision can be made for a device and a method of a gripping mechanism for gripping a puck or a sample tube. A 3D image of the space can be generated during gripping. The sample tube or the position and alignment of the sample tube can be identified on the basis of geometric data, for example the tube center point and/or tube axis. Actuation and gripping can then be carried out in a targeted manner on the basis of these data.

A further camera can be attached to the gripper, to be precise for the fine alignment or compensation of inaccuracies. This camera can be used to find, in two dimensions, a correct attachment point on the tube using the three-dimensional image.

By way of the movement pattern of a gripper finger, it can be possible not only to determine the tube position, but the bearing axis can also be used such that the bearing axis of the tube can be measured and identified. Using this, it can once again be possible to identify how the tube can be gripped best or by how much the position of the gripper may need to be modified in order to correctly grip the tube. Where the next tube can be placed or set down can be already determined during a preceding set down.

Images can be used on the basis of image database analyses in order to establish position and target coordinates and in order to establish a set down point.

Possible damage to the tube can be identified and error messages or different handling procedures can be derived therefrom. It can also be possible to identify damage to a sample carrier which can lead to a different handling of the tube or the whole tube carrier or individual positions of the tube carrier.

A free position can be identified during loading and unloading by way of sampling, where a free grippable position is and, optionally, a desired position is "scooped free" or exposed such that a specific position is ready to be approached.

After successfully placing a sample carrier on a sorting area, the sample carrier can be held by holding devices. The holding device can e.g. be a magnet which can be used, for example, to hold magnetic pucks. However, the holding device can, for example, also be a negative-pressure pump, which can generate a holding effect by generating negative pressure.

Referring initially to FIG. 1, a device for handling sample tubes is shown. It can comprise a 3D camera arrangement 1, by which three-dimensional images can be recorded. The 3D camera arrangement 1 can be arranged in a stationary manner at a predetermined position. Alternatively, it can be arranged in a position-changing manner.

The device can further comprise a gripper apparatus in the form of the gripper 3 for gripping sample tubes 5. The sample tubes 5 can be mounted in a holding apparatus in the form of a tube holder or tube carrier 6. A further camera in the form of a gripper camera 2 can be provided at the gripper 3. The further camera can be a two-dimensional camera.

The tube carrier 6 can rest on a set-down area 7, on which, further, a number of position sensors 8, for example in the form of optical sensors or magnetic sensors, can be arranged. A position of the tube carrier 6 can be established by these position sensors 8. The tube carrier 6 can be fastened to the set-down area 7 by a holding device 9. In one case, these can be magnets.

The gripper 3 can be fastened to an XY positioner 4, by which it can be displaced in two dimensions. For gripping, for the purposes of which raising and lowering are required, it can additionally be moved in a vertical direction.

By the 3D camera arrangement 1, it can be possible to identify positions of the sample tubes 5 and the gripper 3 can be controlled accordingly. By way of example, a specific sample tube 5, which was visually identified thus, can be controlled, gripped and raised. Hence, for example, it can be introduced into an analysis device.

An electronic control apparatus, which can receive images from the 3D camera arrangement 1 and from the gripper camera 2 and which can control the gripper 3 dependently thereon, can serve for control purposes.

By the gripper camera 2, it can be possible to further improve the positioning of the gripper 3 over a respective sample tube 5 and the corresponding gripping.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for automated handling of an unaligned sample tube by a gripper apparatus, wherein the unaligned sample tube is filled with liquid to be analyzed, the method comprises:
    determining a position and alignment of a sample tube in a holding apparatus based on 3D spatial geometric data of the sample tube acquired by an image acquisition apparatus under control of a control apparatus; and
    handling the sample tube by the gripper apparatus under control of the control apparatus, wherein the handling is based on the 3D spatial geometric sample tube position and alignment data acquired by the image acquisition apparatus and conveyed to the control apparatus and wherein upon determination by the image acquisition apparatus that the alignment of the sample tube deviates obliquely from a longitudinal bearing axis standard such that a vertical axis of the sample tube is not parallel to the longitudinal bearing axis, the control apparatus spatially manipulates the gripper apparatus based on the 3D spatial geometric sample tube position and alignment data acquired by the image acquisition apparatus so that the gripper apparatus adjusts itself spatially in order to grip the sample tube obliquely at the same non-parallel deviation from the longitudinal bearing axis standard as the sample tube.

2. The method according to claim 1, wherein when handling the sample tube, the unaligned sample tube is moved by the gripper in terms of its location.

3. The method according to claim 2, wherein when the unaligned sample tube is moved by the gripper in terms of its location, it is lifted.

4. The method according to claim 1, wherein during handling, reformatting is carried out by transferring the sample tube by the gripper from a holding apparatus to a different holding apparatus.

5. The method according to claim 1, wherein during determining the position of the sample tube, a center point of the sample tube is determined in relation to one, two or three dimensions.

6. The method according to claim 1, wherein the image acquisition apparatus is stereo camera or a 3D camera.

7. The method according to claim 1, wherein the determining the position is performed using a further image acquisition apparatus.

8. The method according to claim 7, wherein the further image acquisition apparatus is a 2D camera.

9. The method according to claim 7, wherein the further image acquisition apparatus is assembled on the gripper apparatus.

10. The method according to claim 1, further comprising, identifying a free position in a holding apparatus for sample tubes by the image acquisition apparatus, wherein the sample tube gripped by the gripper apparatus is subsequently set down at the free position by the gripper apparatus.

11. The method according to claim 1, further comprising, identifying damage of the sample tube by the image acquisition apparatus during the step of determining the position, wherein the step of handling of the sample tube is performed depending on whether damage was identified.

12. The method according to claim 1, further comprising, setting down the sample tube at a position from which another sample tube was previously lifted.

13. A device for handling sample tubes, the device comprising:
    a gripper apparatus;
    an image acquisition apparatus; and
    a control apparatus for controlling the gripper apparatus depending on signals generated by the image acquisition apparatus, wherein the control apparatus comprises a processor and storage, wherein instructions are stored in the storage, and wherein the control apparatus is configured to perform the method according to claim 1 when the instructions are executed by the processor.

14. The device according to claim 13, wherein the image acquisition apparatus comprises a stereo camera or a 3D camera arranged stationary in space, and wherein the image acquisition apparatus further comprises a 2D camera arranged at the gripper apparatus and displaced from the 3D camera.

15. The device according to claim 13, wherein the gripper apparatus is displaceable in two dimensions by being fastened to an XY-positioner.

* * * * *